(12) United States Patent
Matheny (10) Patent No.: US 9,381,218 B2
(45) Date of Patent: Jul. 5, 2016

(54) ARTIFICIAL SKELETAL MATERIAL AND CONSTRUCTS FORMED THEREFROM

(71) Applicant: Robert G Matheny, Norcross, GA (US)

(72) Inventor: Robert G Matheny, Norcross, GA (US)

(73) Assignee: CerMatrix Cardiovascular, Inc., Roswell, GA (US)

(*) Notice: Subject to any disclaimer, the term of this patent is extended or adjusted under 35 U.S.C. 154(b) by 0 days.

(21) Appl. No.: 14/223,833

(22) Filed: Mar. 24, 2014

(65) Prior Publication Data

US 2015/0265653 A1  Sep. 24, 2015

(51) Int. Cl.

| A61F 2/00 | (2006.01) |
|---|---|
| A61K 35/12 | (2015.01) |
| A61K 35/32 | (2015.01) |
| A61K 35/28 | (2015.01) |
| A61K 45/06 | (2006.01) |
| A61K 35/545 | (2015.01) |
| A61L 27/36 | (2006.01) |
| A61L 27/38 | (2006.01) |
| A61L 27/54 | (2006.01) |
| A61F 2/28 | (2006.01) |

(52) U.S. Cl.
CPC ............... *A61K 35/32* (2013.01); *A61K 35/28* (2013.01); *A61K 35/545* (2013.01); *A61K 45/06* (2013.01); *A61L 27/365* (2013.01); *A61L 27/3608* (2013.01); *A61L 27/3633* (2013.01); *A61L 27/3834* (2013.01); *A61L 27/3847* (2013.01); *A61L 27/54* (2013.01); *A61F 2/28* (2013.01); *A61L 2300/252* (2013.01); *A61L 2300/406* (2013.01); *A61L 2300/414* (2013.01); *A61L 2300/64* (2013.01); *A61L 2430/02* (2013.01)

(58) Field of Classification Search
CPC ...... A61F 2/28; A61K 35/28; A61L 27/3633; A61L 27/365; A61L 2300/252; A61L 2300/414; A61L 2430/02
USPC .................................. 424/423, 426, 549, 572
See application file for complete search history.

(56) References Cited

U.S. PATENT DOCUMENTS

| 4,356,261 A | 10/1982 | Kuettner |
| 7,718,616 B2 | 5/2010 | Thorne |
| 8,323,722 B2 | 12/2012 | Rabiei |

OTHER PUBLICATIONS

Suokas et al., 2007, US 20070141111 A1.*
Gisselfaelt, Katrin, 2006, Medical Plastics 2006, Collected Papers of the International Conference and Seminar, 20th, Copenhagen, Denmark, Nov. 27-30, 2006, Abstract.*
Hwang et al., 2012, US 20120253464 A1.*
Bahuleyan B., et al., Evaluation of a Series of Scaffolds for Osteoinduction Using rh BMP-2 in Athymic Rats, Plastic and Reconstructive Surgery, Oct. 2009, p. 4, vol. 124(4S).
Bose S., et al., Trends in Biotechnology, Recent Advances in Bone Tissue Engineering Scaffolds. Trends Biotechnology, Oct. 2012, p. 546-554, vol. 30(10).

* cited by examiner

*Primary Examiner* — Shin Lin Chen
(74) *Attorney, Agent, or Firm* — Francis Law Group (57) ABSTRACT

A bioresorbable skeletal construct member formed from an osteoinductive composition comprising autogenic bone and an extracellular matrix (ECM) material, the construct member being configured to induce osteoanagenesis and angiogenesis when implanted proximate endogenous bone and tissue.

8 Claims, 1 Drawing Sheet

ARTIFICIAL SKELETAL MATERIAL AND CONSTRUCTS FORMED THEREFROM

FIELD OF THE INVENTION

The present invention generally relates to artificial skeletal structures. More particularly, the present invention relates to extracellular matrix (ECM) based osteoinductive skeletal material and bioresorbable, osteoinductive and osteoconductive skeletal constructs formed therefrom.

BACKGROUND OF THE INVENTION

As is well known in the art, when bone is damaged or removed as a result of trauma or surgery, e.g., excision of a tumor, new bone must be regenerated or substituted with a prosthetic skeletal structure, e.g. skeletal prosthesis or construct, or bone substitute material.

Ideally, the prosthetic skeletal structure and/or bone substitute material is derived from calcified autogenic bone material. However, the availability of autogenic bone material and the risks of allogenic bone initiating an immunologic rejection makes the use of natural bone material and structures formed therefrom impractical and expensive for widespread use.

Various alternative materials have thus been developed to form bone substitute compositions and prosthetic skeletal constructs, such as calcium phosphate ceramic materials (i.e. bioceramics), composite materials, bone derivatives, metals, and natural and synthetic polymers.

Calcium phosphate ceramic materials; particularly, hydroxyapatites (HAp) have been widely employed in prosthetic applications for several years. The suitability of HAp as a prosthetic material stems from the facts that it is relatively easy and cheap to manufacture, is nontoxic, and appears to attach well to calcified tissues. Moreover, HAp has the advantageous property of being able to conduct bone apposition, i.e. the bone remodeling process that initially establishes fixation of an uncemented prosthetic structure to adjacent bone.

There are, however, several drawbacks and disadvantages associated with the use of calcium phosphate ceramic materials. Unsintered calcium phosphate prosthetic structures lack sufficient compressive strength and load bearing capacity to be of substantial benefit as a load bearing prosthesis. Further, sintered calcium phosphate ceramics, while able to bear higher compressive forces, are typically too brittle, and not of sufficient porosity to enable cellular and vascular infiltration of the prosthetic structure to the extent necessary to promote remodeling and resorbtion of the structure.

Various metals; particularly, titanium and titanium alloys, have also been widely employed in prosthetic applications. Titanium is, of course, highly biocompatible and exhibits excellent mechanical properties.

Metal and metal composite prostheses are typically rendered more biocompatible by coating the surface thereof with biocompatible materials, such as crystalline HAp, which has the further advantage of being able to serve as a pharmacological carrier medium. However, HAp crystals are not easily grown on the surface of metal prostheses; particularly, under the physiological conditions required to retain biological activity of some bioactive agents used in orthopedic applications.

Various synthetic materials have also been employed to form prosthetic skeletal constructs. The most prevalent synthetic materials that are employed are mixtures of polymethylmetachlorite (PMMA) and benzoilperoxide.

There are similarly several drawbacks and disadvantages associated with the use of synthetic materials. A major drawback is that synthetic materials do not degrade naturally in vivo. Thus, newly growing bone is obstructed by the artificial constructs, resulting in inflammed neighboring tissues.

A further major drawback of synthetic materials is that many synthetic materials can, and in many instances will, induce or elicit an inflammatory response.

There is thus a need to provide improved bone substitute material and bioresorbable skeletal constructs having sufficient compressive strength and load bearing capacity to be employed in load bearing applications without the drawbacks associated with metal, ceramic and polymeric materials.

It is therefore an object of the present invention to provide bone substitute material and bioresorbable skeletal constructs that overcome the foregoing and the other disadvantages associated with prior art bone substitution materials and prosthetic structures.

It is another object of the present invention to provide a novel extracellular matrix (ECM) based osteoinductive, biodegradable bone substitute material that promotes biocompatible osteoanagenesis.

It is another object of the present invention to provide a novel ECM based bone substitution material that is suitable for use in osteoanagenesis and bone morphogenesis.

It is another object of the present invention to provide a novel ECM based bone substitution material that exhibits satisfactory biocompatibility, osteoinductivity, osteoconductivity, biodegradability, with freedom from immunogenicity and toxicity to tissues.

It is yet another object of the present invention to provide artificial bioresorbable, skeletal constructs that promote angiogenesis.

It is yet another object of the present invention to provide artificial bioresorbable, osteoconductive and osteoinductive skeletal constructs that promote osteoanagenesis.

It is yet another object of the present invention to provide artificial bioresorbable, osteoconductive and osteoinductive skeletal constructs that function as delivery platforms for pharmacological agents and compositions.

SUMMARY OF THE INVENTION

The present invention is directed to novel extracellular matrix (ECM) based osteoinductive, biodegradable bone substitute material that promotes osteoanagenesis and, in some aspects, angiogenesis, and porous, bioresorbable, osteoinductive and osteoconductive skeletal constructs formed therefrom.

In a preferred embodiment of the invention, the ECM based bone substitute material comprises a composite material that includes a base material or component and an ECM material.

According to the invention, the base material can comprise various natural and biocompatible synthetic materials, including, without limitation, autogenic bone, bone particulate, and calcium containing mineral compounds. In a preferred embodiment of the invention, the base material comprises autogenic bone, more preferably, particulate autogenic bone.

According to the invention, the autogenic bone can be prepared by various conventional means, including dry milling, pulverizing, grinding and cutting.

In some embodiments of the invention, at least 50% of the particulate bone has a particle size in the range of 50-5000 microns. In some embodiments, at least 50% of the particulate bone has a particle size no greater than 2000 microns.

According to the invention, the ECM material can be derived from various mammalian tissue sources including, without limitation, small intestinal submucosa, stomach submucosa, large intestinal tissue, urinary bladder submucosa, cardiac tissue, e.g., pericardium, epicardium, endocardium and/or myocardium tissue, dura tissue, skin tissue, lung tissue, kidney tissue, pancreatic tissue, prostate tissue, mesothelial tissue, nervous system tissue, fetal tissue, placenta tissue, ureter tissue, cardiovascular tissue, e.g., veins and arteries, heart valves with or without their attached vessels, tissue surrounding the roots of developing teeth, tissue surrounding growing bone, and combinations thereof.

The ECM material can also be derived from basement membrane of mammalian tissue/organs, including, without limitation, urinary bladder membrane, liver basement membrane, amnion, chorion, allograft pericardium, allograft acellular dermis, amniotic membrane, Wharton's jelly and combinations thereof.

The ECM material can also be derived from other sources, including, without limitation, collagen from animal and plant sources, and synthesized extracellular matrices, i.e. cell cultures.

In some embodiments, the ECM material includes one or more additional biologically active agents or components to facilitate the healing of damaged or diseased bone and/or enhance the bone regenerative process.

In some embodiments of the invention, the biologically active agent comprises an osteogenic agent. In some embodiments, the osteogenic agent is selected from the group comprising, without limitation, polypeptide growth factors, such as, osteogenin, insulin-like growth factor (IGF)-1, TGF-β1, TGF-β2, TGF-β3, TGF-β4, TGF-β5, osteoinductive factor (OIF), basic fibroblast growth factor (bFGF), acidic fibroblast growth factor (aFGF), platelet-derived growth factor (PDGF), vascular endothelial growth factor (VEGF), growth hormone (GH), osteogenic protein-1 (OP-1).

In some embodiment of the invention, the biologically active agent comprises a bone protein. In some embodiments, the bone protein is selected from the group comprising, without limitation, alkaline phosphatase, osteocalcin, bone sialoprotein (BSP) and osteocalcin in secreted phosphoprotein (SPP)-1, type I collagen, type IV collagen, fibronectin, osteonectin, thrombospondin, matrix-gla-protein, SPARC, alkaline phosphatase and osteopontin.

In some embodiment of the invention, the biologically active agent comprises a bone morphogenic protein (BMP). In some embodiments, the bone morphogenic protein is selected from the group comprising, without limitation, BMP-1, BMP-2, BMP-2A, BMP-2B, BMP-3, BMP-3b, BMP-4, BMP-5, BMP-6, BMP-7, BMP-8, BMP-8b, BMP-9, BMP-10, BMP-11, BMP-12, BMP-13, BMP-14, BMP-15.

In some embodiments of the invention, the biologically active agent comprises a cell selected from the group comprising, without limitation, a myofibroblast, mesenchymal stem cell, autotransplanted expanded cardiomyocyte, adipocyte, totipotent cell, pluripotent cell, blood stem cell, myoblast, adult stem cell, bone marrow cell, mesenchymal cell, embryonic stem cell, parenchymal cell, epithelial cell, endothelial cell, mesothelial cell, fibroblast, myofibroblast, osteoblast, chondrocyte, exogenous cell, endogenous cell, stem cell, hematopoetic stem cell, pluripotent stem cell, bone marrow-derived progenitor cell, progenitor cell, myocardial cell, skeletal cell, undifferentiated cell, multi-potent progenitor cell, unipotent progenitor cell, monocyte, cardiomyocyte, cardiac myoblast, skeletal myoblast, macrophage, capillary endothelial cell, xenogenic cell, and allogenic cell.

In some embodiments of the invention, the biologically active agent comprises a growth factor selected from the group comprising, without limitation, a platelet derived growth factor (PDGF), epidermal growth factor (EGF), transforming growth factor alpha (TGF-alpha), fibroblast growth factor-2 (FGF-2), hepatocyte growth factor (HGF), nerve growth factor (NGF), tumor necrosis factor alpha (TNA-alpha), and placental growth factor (PLGF), and VEGF family.

In some embodiments of the invention, the biologically active agent comprises an analgesic agent selected from the group comprising, without limitation, norepinephrine, bupivacaine, ropivacaine, 2-chloroprocaine, lidocaine, mepivacaine, ropivacaine, mepivacaine, benzocaine, tetracaine, dibucaine, cocaine, prilocaine, dibucaine, procaine, chloroprocaine, prilocaine, mepivacaine, etidocaine, tetracaine, xylocaine, morphine, fentanyl, alphaxalone and active analogs, 5-alpha-pregnane-3 alpha-21-diol-20-one (tetrahydrodeoxycorticosterone or THDOC), allotetrahydrocortisone, dehydroepiandrosterone, benzodiapenes, nifedipine, nitrendipine, verapamil, aminopyridine, benzamil, diazoxide, 5,5 diphenylhydantoin, minoxidil, tetrethylammonium, valproic acid, aminopyrine, phenazone, dipyrone, apazone, phenylbutazone, clonidine, taxol, colchicines, vincristine, vinblastine, levorphanol, racemorphan, levallorphan, dextromethorphan, cyclorphan, butorphanol, codeine, heterocodeine, morphinone, dihydromorphine, dihydrocodeine, dihydromorphinone, dihydrocodeinone, 6-desoxymorphine, heroin, oxymorphone, oxycodone, 6-methylene-dihydromorphine, hydrocodone, hydromorphone, metopon, apomorphine, normorphine, N-(2-phenylethyl)-normorphine, etorphine, buprenorphine, phenazocine, pentazocine and cyclazocine, meperidine, diphenoxylate, ketobemidone, anileridine, piminodine, fentanil, ethoheptazine, alphaprodine, betaprodine, 1-methyl-4-phenyl-1,2,5,6-tetrahydropyridine (MPTP), loperamide, sufentanil, alfentanil, remifentanil, lofentanil, 6,7-benzomorphans, ketazocine, aryl-acetamides, U-50,488, spiradoline (U-62,066), enadoline (CI-977), asimadoline, EMD-61753, naltrexone, naltrindole.

In some embodiments of the invention, the biologically active agent comprises an antibiotic agent selected from the group comprising, without limitation, tylosin tartrate, tylosin, oxytetracycline, tilmicosin phosphate, ceftiofur hydrochloride, ceftiofur sodium, sulfadimethoxine cefamandole, tobramycin, penicillin, cefoxitin, oxacillin, vancomycin, cephalosporin C, cephalexin, cefaclor, cefamandole, ciprofloxacin, bisphosphonates, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, magainins, cathelocedins, and defensins.

In some embodiments of the invention, the biologically active agent comprises an anti-inflammatory agent selected from the group comprising, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium. In some embodiments of the invention, the biologically active agent comprises a statin selected from the group comprising atorvastatin, cerivastatin, fluvastatin, lovastatin, mevastatin, pitavastatin, pravastatin, rosuvastatin, and simvastatin.

In some embodiments of the invention, the biologically active agent comprises chitosan.

As indicated above, the present invention is also directed to porous, bioresorbable, osteoinductive and osteoconductive skeletal constructs formed with the ECM based bone substitute material of the invention.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

DEFINITIONS

The term "bioresorbable," as used herein, means and includes a biocompatible material, composition or object that has the ability to be gradually integrated into a host. When used in the context of the skeletal constructs (or bone implants) of the invention, the term generally refers to the ability of at least a portion of a skeletal construct to gradually be replaced by natural bone, such replacement typically occurring naturally by the physiological process of bone remodeling. Thus, in the context of the presently described embodiments, the term "bioresorbable" is meant to include any material or process that is receptive to or typically associated with bone remodeling, including, but not limited to osteoblast and osteoclast activity, deposition and/or mineralization of new bone matrix, vascular and cellular infiltration and tissue ingrowth.

The term "osteoanagenesis," as used herein, means and includes the regeneration of bone tissue.

The term "osteoconductive," as used herein, means and includes a structure that facilitates or supports the growth of new bone tissue. Preferably, native osteoblasts and other components utilize the osteoconductive structure as a framework upon which to spread and generate new bone.

The term "osteoinductive," as used herein, means and includes a structure, material or composition that induces and/or supports the formation, development and growth of new bone, and/or the remodeling of existing bone.

The term "osteogenic agent," as used herein, means and includes an active agent that can elicit, facilitate and/or maintain the formation and growth of bone tissue. Many osteogenic agents function, at least in part, by stimulating or otherwise regulating the activity of osteoblast and/or osteoclasts. Exemplary osteogenic agents include, without limitation, certain polypeptide growth factors, such as, osteogenin, Insulin-like Growth Factor (IGF)-1, TGF-β1, TGF-β2, TGF-β3, TGF-β4, TGF-β5, osteoinductive factor (OIF), basic Fibroblast Growth Factor (bFGF), acidic Fibroblast Growth Factor (aFGF), Platelet-Derived Growth Factor (PDGF), vascular endothelial growth factor (VEGF), Growth Hormone (GH), osteogenic protein-1 (OP-1) and any one of the many known bone morphogenic proteins (BMPs), including but not limited to BMP-1, BMP-2, BMP-2A, BMP-2B, BMP-3, BMP-3b, BMP-4, BMP-5, BMP-6, BMP-7, BMP-8, BMP-8b, BMP-9, BMP-10, BMP-11, BMP-12, BMP-13, BMP-14, BMP-15.

The terms "cortical portion" and "cortical" are used interchangeably herein, and mean and include a portion of a skeletal construct that functions in a load-bearing capacity and whose function and structure are substantially similar to that of naturally occurring cortical or compact bone.

The terms "cancellous portion" and "cancellous" are used interchangeably herein, and mean and include portions of a skeletal construct that is more porous than the cortical portion, and whose structure and function of which are substantially similar to that of naturally occurring trabecular or spongy bone. Due to its high degree of porosity, a cancellous portion has a relatively high surface area and can support tissue ingrowth and infiltration of body fluids and cells.

The terms "bone morphogenic protein" and "BMP" are used interchangeably herein, and mean and include a group of polypeptide growth factors belonging to the TGF-β superfamily. BMPs are widely expressed in many tissues, though many function, at least in part, by influencing the formation, maintenance, structure or remodeling of bone or other calcified tissues.

The term "bone protein," as used herein, means and includes a polypeptide factor that supports the growth, remodeling, mineralization or maintenance of calcified tissues. Bone proteins are typically components of or associate with cells and structures that form extracellular matrix structures. Typical examples of bone proteins include, without limitation, alkaline phosphatase, osteocalcin, bone sialoprotein (BSP) and osteocalcin in secreted phosphoprotein (SPP)-1, type I collagen, type IV collagen, fibronectin, osteonectin, thrombospondin, matrix-gla-protein, SPARC, alkaline phosphatase and osteopontin.

The terms "extracellular matrix," "extracellular matrix material" and "ECM" are used interchangeably herein, and mean and include a collagen-rich substance that is found in between cells in animal tissue and serves as a structural element in tissues. According to the invention, extracellular matrix material can be isolated or derived from various mammalian tissue sources including, without limitation, small intestinal submucosa, stomach submucosa, large intestinal tissue, urinary bladder submucosa, cardiac tissue, e.g., pericardium, epicardium, endocardium and/or myocardium tissue, dura tissue, skin tissue, lung tissue, kidney tissue, pancreatic tissue, prostate tissue, mesothelial tissue, nervous system tissue, fetal tissue, placenta tissue, ureter tissue, cardiovascular tissue, e.g., veins and arteries, heart valves with or without their attached vessels, tissue surrounding the roots of developing teeth, tissue surrounding growing bone, and combinations thereof.

Extracellular matrix material can also be derived from basement membrane of mammalian tissue/organs, including, without limitation, urinary bladder membrane, liver basement membrane, amnion, chorion, allograft pericardium, allograft acellular dermis, amniotic membrane, Wharton's jelly and combinations thereof.

Extracellular matrix material can also be derived from other sources, including, without limitation, collagen from animal and plant sources, and synthesized extracellular matrices, i.e. cell cultures.

The term "angiogenesis," as used herein, means a physiologic process involving the growth of new blood vessels from pre-existing blood vessels.

The term "neovascularization," as used herein, means and includes the formation of functional vascular networks that can be perfused by blood or blood components. Neovascularization includes angiogenesis, budding angiogenesis, intussuceptive angiogenesis, sprouting angiogenesis, therapeutic angiogenesis and vasculogenesis.

The terms "pharmacological agent," "active agent," "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent," "active agent," "drug" and "active agent formulation" thus mean and include, without limitation, antibiotics, anti-viral agents, analgesics, steroidal anti-inflammatories, non-steroidal anti-inflammatories, anti-neoplastics, anti-spasmodics, modulators of cell-extracellular matrix interactions, hormones, growth factors, matrix metalloproteinases (MMPS), enzymes and enzyme inhibitors, anticoagulants, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent," "active agent," "drug" and "active agent formulation" thus include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, Anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

According to the invention, the terms "pharmacological agent," "active agent," "drug" and "active agent formulation" can further include, without limitation, the following growth factors: platelet derived growth factor (PDGF), epidermal growth factor (EGF), transforming growth factor alpha (TGF-alpha), transforming growth factor beta (TGF-beta), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platlet derived growth factor (PDGF), tumor necrosis factor alpha (TNA-alpha), and placental growth factor (PLGF).

The terms "pharmacological agent," "active agent," "drug" and "active agent formulation" further mean and include, without limitation, the following antibiotics: tylosin tartrate, tylosin, oxytetracycline, tilmicosin phosphate, ceftiofur hydrochloride, ceftiofur sodium, sulfadimethoxine cefamandole, tobramycin, penicillin, cefoxitin, oxacillin, vancomycin, cephalosporin C, cephalexin, cefaclor, cefamandole, ciprofloxacin, bisphosphonates, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione.

The terms "pharmacological agent," "active agent," "drug" and "active agent formulation" further include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "pharmacological agent," "active agent," "drug" and "active agent formulation" can further include, without limitation, the following analgesics: norepinephrine, bupivacaine, ropivacaine, 2-chloroprocaine, lidocaine, mepivacaine, ropivacaine, mepivacaine, benzocaine, tetracaine, dibucaine, cocaine, prilocaine, dibucaine, procaine, chloroprocaine, prilocaine, mepivacaine, etidocaine, tetracaine, xylocaine, morphine, fentanyl, alphaxalone and active analogs, 5-alpha-pregnane-3 alpha-21-diol-20-one (tetrahydrodeoxycorticosterone or THDOC), allotetrahydrocortisone, dehydroepiandrosterone, benzodiapenes, nifedipine, nitrendipine, verapamil, aminopyridine, benzamil, diazoxide, 5,5 diphenylhydantoin, minoxidil, tetrethylammonium, valproic acid, aminopyrine, phenazone, dipyrone, apazone, phenylbutazone, clonidine, taxol, colchicines, vincristine, vinblastine, levorphanol, racemorphan, levallorphan, dextromethorphan, cyclorphan, butorphanol, codeine, heterocodeine, morphinone, dihydromorphine, dihydrocodeine, dihydromorphinone, dihydrocodeinone, 6-desoxymorphine, heroin, oxymorphone, oxycodone, 6-methylene-dihydromorphine, hydrocodone, hydromorphone, metopon, apomorphine, normorphine, N-(2-phenylethyl)-normorphine, etorphine, buprenorphine, phenazocine, pentazocine and cyclazocine, meperidine, diphenoxylate, ketobemidone, anileridine, piminodine, fentanil, ethoheptazine, alphaprodine, betaprodine, 1-methyl-4-phenyl-1,2,5,6-tetrahydropyridine (MPTP), loperamide, sufentanil, alfentanil, remifentanil, lofentanil, 6,7-benzomorphans, ketazocine, aryl-acetamides, U-50,488, spiradoline (U-62,066), enadoline (CI-977), asimadoline, EMD-61753, naltrexone, naltrindole.

The terms "pharmacological agent," "active agent," "drug" and "active agent formulation" can further include one or more classes of topical or local anesthetics, including, without limitation, esters, such as benzocaine, chloroprocaine, cocaine, cyclomethycaine, dimethocaine/larocaine, piperocaine, propoxycaine, procaine/novacaine, proparacaine, and tetracaine/amethocaine. Local anesthetics can also include, without limitation, amides, such as articaine, bupivacaine, cinchocaine/dibucaine, etidocaine, levobupivacaine, lidocaine/lignocaine, mepivacaine, prilocaine, ropivacaine, and trimecaine. Local anesthetics can further include combinations of the above from either amides or esters.

The terms "pharmacological agent," "active agent," "drug" and "active agent formulation" can further include one or more classes of cytotoxic anti-neoplastic agents or chemotherapy agents, including, without limitation, alkylating agents, cisplatin, carboplatin, oxaliplatin, mechlorethamine, cyclophosphamide, chlorambucil, and ifosfamide. Chemotherapy agents can also include, without limitation, antimetabolites, such as purine analogues, pyrimidine analogues, and anti folates. Chemotherapy drugs can also include, without limitation, plant alkaloids, such as vincristine, vinblastine, vinorelbine, vindesine, podophyllotoxin, etoposide, teniposide, taxanes, such as paclitaxel and docetaxel, topoisomerase inhibitors, such as irinotecan, topotecan, amsacrine, etoposide, etoposide phosphate and teniposide, cytotoxic antibiotics, such as actinomyocin, bleomycin, plicamycin, mytomycin and anthracyclines, such as doxorubicin, daunorubicin, valrubicin, idarubicin, epirubicin, and antibody treatments, such as abciximab, adamlimumab, alamtuzumab, basiliximab, belimumab, bevacizumab, brentuximab vedotin, canakinumab, cetuximab, certolizumab pego, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumumab, ranibizumab, rituximab, tocilizumab (atlizumab), tositumomab and trastuzumab.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation, i.e. the protective tissue response to injury or destruction of tissues, which serves to destroy, dilute, or wall off both the injurious agent and the injured tissues.

Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclofenac, cintazone, cliprofen, clobetasol propionate, clobetasone butyrate, clopirac, cloticasone propionate, connethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The terms "cells" and "stem cells" are also used interchangeably herein, and mean and include an organism that has the potential to induce modulating proliferation, and/or growth and/or regeneration of tissue. Stem cells can thus include, without limitation, human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stein cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

According to the invention, the terms "pharmacological agent," "active agent," "drug" and "active agent formulation" can further include the following active agents (referred to interchangeably herein as a "protein", "peptide" and "polypeptide"): collagen (types I-V), proteoglycans, glycosaminoglycans (GAGs), glycoproteins, growth factors, cytokines, cell-surface associated proteins, cell adhesion molecules (CAM), angiogenic growth factors, endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/enactins, fibulin I, finulin II, integrins, transmembrane molecules, thrombospondins, osteopontins, and angiotensin converting enzymes (ACE).

The term "biologically active composition" and "osteoinductive composition" are used interchangeably herein, and mean and include a composition that is capable of inducing or affecting an action in a biological system, e.g. by inducing or affecting a therapeutic or prophylacetic effect, an immune response, tissue growth, cell growth, cell differentiation or cell proliferation.

According to the invention, a biologically active and/or osteoinductive composition can also comprise or include an active agent delivery vehicle. The delivery vehicle would typically be optimized to stably accommodate an effective dosage of one or more biologically active or pharmacological agents of the invention. The determination of the effective dose of a biologically active or pharmacological agent that should be included in a biologically active and/or osteoinductive composition to achieve a desired biological response is dependent on the particular agent, the magnitude of the desired response, and the physiological context of the composition. Such determinations may be readily made by an ordinary practitioner of the pharmaceutical arts.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The tenor "adolescent", as used herein, means and includes a mammal, i.e. a mammalian tissue or cell source, which is less than two (2) years of age.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to extracellular matrix (ECM) based osteoinductive, biodegradable bone substitute material that promotes angiogenesis, and porous, bioresorbable, osteoinductive and osteoconductive skeletal constructs formed therefrom. According to the invention, the skeletal constructs of the invention can be readily employed to replace or support, e.g., bone over-lays or grafts, diseased, defective or missing bone in the body.

ECM Based Bone Substitute Material

In a preferred embodiment of the invention, the ECM based bone substitute material comprises an osteoinductive, biodegradable composite material, i.e. an osteoinductive composition, that includes a base material or component and an ECM material.

In some embodiments of the invention, the osteoinductive composition comprises at least 20% ECM. In some embodiments, the osteoinductive composition comprises at least 50% ECM.

According to the invention, the ECM based bone substitute material can comprises various forms, including, without limitation, a fluidized material, paste, putty, gel, etc.

According to the invention, the base material can comprise various natural and biocompatible materials, including, without limitation, autogenic bone, bone particulates, and calcium containing mineral compounds.

In some embodiments of the invention, the base material comprises bone marrow; preferably, bone marrow derived from heme producing bones. According to the invention, the bone marrow functions as a central supply for circulating cells; particularly, progenitor cells, which transition to stem cells.

In some embodiments of the invention, the base material comprises Artelon®, a degradeable polyurethane manufactured by Artimplant AB, Vastra Frolunda, Sweden.

In a preferred embodiment of the invention, the base material comprises autogenic bone, more preferably, particulate autogenic bone.

According to the invention, the autogenic bone can be prepared by various conventional means, including dry milling, pulverizing, grinding and cutting.

In some embodiments of the invention, at least 50% of the particulate bone has a particle size in the range of 50-5000 microns. In some embodiments, at least 50% of the particulate bone has a particle size no greater than 2000 microns.

According to the invention, the ECM material can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety. Thus, in some embodiments of the invention, the mammalian tissue source includes, without limitation, small intestinal submucosa, stomach submucosa, large intestinal tissue, urinary bladder submucosa, cardiac tissue, e.g., pericardium, epicardium, endocardium and/or myocardium tissue, dura tissue, skin tissue, lung tissue, kidney tissue, pancreatic tissue, prostate tissue, mesothelial tissue, nervous system tissue, fetal tissue, placenta tissue, ureter tissue, cardiovascular tissue, e.g., veins and arteries, heart valves with or without their attached vessels, tissue surrounding the roots of developing teeth, tissue surrounding growing bone, and combinations thereof.

The terms "small intestinal submucosa," "stomach submucosa" and "urinary bladder submucosa" also mean and include any small intestinal submucosa and/or stomach submucosa and/or urinary bladder submucosa that includes the tunica mucosa (which includes the transitional epithelial layer and the tunica propria), submucosal layer, one or more layers of muscularis, and adventitia associated therewith.

The ECM material can also be derived from basement membrane of mammalian tissue/organs, including, without limitation, urinary bladder membrane, liver basement membrane, amnion, chorion, allograft pericardium, allograft acellular dermis, amniotic membrane, Wharton's jelly and combinations thereof.

Additional sources of mammalian basement membrane include, without limitation, spleen, lymph nodes, salivary glands, prostate, pancreas and other secreting glands.

The ECM material can also be derived from other sources, including, without limitation, collagen from animal and plant sources, and synthesized extracellular matrices, i.e. cell cultures.

According to the invention, the ECM material can comprise, in whole or in part, just the basement membrane (or transitional epithelial layer) with the subadjacent tunica propria, the tunica submucosa, tunica muscularis, and tunica serosa. The ECM material can contain any or all of these layers, and thus could conceivably contain only the basement membrane portion, excluding the submucosa. However, generally, and especially since the submucosa is thought to contain and support the active growth factors, cytokines and other proteins necessary for in vivo tissue regeneration, the ECM material from any given tissue source will contain the active extracellular matrix portions that support cell development and differentiation and tissue regeneration.

In a preferred embodiment, the ECM material is derived from adolescent, i.e. less than 3 years of age, mammalian tissue.

In some embodiments, the ECM material includes one or more additional biologically active agents, which support the formation, development and growth of new bone, and/or the remodeling thereof.

Thus, in some embodiments of the invention, the biologically active agent comprises an osteoinductive agent or compound. According to the invention, suitable osteoinductive compounds include, without limitation, osteogenic agents and compounds.

In some embodiments of the invention, the biologically active agent thus comprises, without limitation, one or more of the following osteogenic agents: osteogenin, insulin-like growth factor (IGF)-1, TGF-β1, TGF-β2, TGF-β3, TGF-β4, TGF-β5, osteoinductive factor (OIF), basic fibroblast growth factor (bFGF), acidic fibroblast growth factor (aFGF), platelet-derived growth factor (PDGF), vascular endothelial growth factor (VEGF), growth hormone (GH), osteogenic protein-1 (OP-1).

In some embodiments of the invention, the biologically active agent comprises a bone morphogenic protein (BMP). In some embodiments, the bone morphogenic protein is selected from the group comprising, without limitation, BMP-1, BMP-2, BMP-2A, BMP-2B, BMP-3, BMP-3b, BMP-4, BMP-5, BMP-6, BMP-7, BMP-8, BMP-8b, BMP-9, BMP-10, BMP-11, BMP-12, BMP-13, BMP-14, BMP-15.

Additional agents and compounds that support the formation, development and growth of new bone and/or the remodeling thereof include bone matrix proteins and cells.

Thus, in some embodiments of the invention, the biologically active agent comprises a bone matrix protein. According to the invention, suitable bone matrix proteins include, without limitation, alkaline phosphatase, osteocalcin, bone sialoprotein (BSP) and osteocalcin in secreted phosphoprotein (SPP)-1, type I collagen, type IV collagen, fibronectin, osteonectin, thrombospondin, matrix-gla-protein, SPARC, alkaline phosphatase and osteopontin.

In some embodiments of the invention, the biologically active agent comprises a cell. According to the invention, suitable cells include, without limitation, myofibroblast, mesenchymal stem cell, autotransplanted expanded cardiomyocyte, adipocyte, totipotent cell, pluripotent cell, blood stem cell, myoblast, adult stem cell, bone marrow cell, mesenchymal cell, embryonic stem cell, parenchymal cell, epithelial cell, endothelial cell, mesothelial cell, fibroblast, myofibroblast, osteoblast, chondrocyte, exogenous cell, endogenous cell, stem cell, hematopoetic stem cell, pluripotent stem cell, bone marrow-derived progenitor cell, progenitor cell, myocardial cell, skeletal cell, undifferentiated cell, multi-potent progenitor cell, unipotent progenitor cell, monocyte, cardiomyocyte, cardiac myoblast, skeletal myoblast, macrophage, capillary endothelial cell, xenogenic cell, and allogenic cell.

In some embodiments of the invention, the biologically active agent comprises one or more of the following additional growth factors: a platelet derived growth factor (PDGF), epidermal growth factor (EGF), transforming growth factor alpha (TGF-alpha), fibroblast growth factor-2 (FGF-2), hepatocyte growth factor (HGF), nerve growth factor (NGF), tumor necrosis factor alpha (TNA-alpha), and placental growth factor (PLGF).

In some embodiments of the invention, the aforementioned BMPs, growth factors and cells are derived from adolescent sources.

According to the invention, the biologically active agent may, in some embodiments, comprise one of the aforementioned pharmacologically active agents or compounds that do not act locally to stimulate bone growth and healing, but that nonetheless are capable of producing a desired biological effect in vivo, e.g., stimulation or suppression of an immune response, anti-bacterial activity, etc.

Thus, in some embodiments of the invention, the biologically active agent comprises an analgesic agent. According to the invention, suitable analgesic agents include, without limitation, norepinephrine, bupivacaine, ropivacaine, 2-chloroprocaine, lidocaine, mepivacaine, ropivacaine, mepivacaine, benzocaine, tetracaine, dibucaine, cocaine, prilocaine, dibucaine, procaine, chloroprocaine, prilocaine, mepivacaine, etidocaine, tetracaine, xylocaine, morphine, fentanyl, alphaxalone and active analogs, 5-alpha-pregnane-3 alpha-21-diol-20-one (tetrahydro-deoxycorticosterone or THDOC), allotetrahydrocortisone, dehydroepiandrosterone, benzodiapenes, nifedipine, nitrendipine, verapamil, aminopyridine, benzamil, diazoxide, 5,5 diphenylhydantoin, minoxidil, tetrethylammonium, valproic acid, aminopyrine, phenazone, dipyrone, apazone, phenylbutazone, clonidine, taxol, colchicines, vincristine, vinblastine, levorphanol, racemorphan, levallorphan, dextromethorphan, cyclorphan, butorphanol, codeine, heterocodeine, morphinone, dihydromorphine, dihydrocodeine, dihydromorphinone, dihydrocodeinone, 6-desoxymorphine, heroin, oxymorphone, oxycodone, 6-methylene-dihydromorphine, hydrocodone, hydromorphone, metopon, apomorphine, normorphine, N-(2-phenylethyl)-normorphine, etorphine, buprenorphine, phenazocine, pentazocine and cyclazocine, meperidine, diphenoxylate, ketobemidone, anileridine, piminodine, fentanil, ethoheptazine, alphaprodine, betaprodine, 1-methyl-4-phenyl-1,2,5,6-tetrahydropyridine (MPTP), loperamide, sufentanil, alfentanil, remifentanil, lofentanil, 6,7-benzomorphans, ketazocine, aryl-acetamides, U-50,488, spiradoline (U-62,066), enadoline (CI-977), asimadoline, EMD-61753, naltrexone, naltrindole.

In some embodiments of the invention, the biologically active agent comprises an antibiotic agent. According to the invention, suitable antibiotic agents include, without limitation, tylosin tartrate, tylosin, oxytetracycline, tilmicosin phosphate, ceftiofur hydrochloride, ceftiofur sodium, sulfadimethoxine cefamandole, tobramycin, penicillin, cefoxitin, oxacillin, vancomycin, cephalosporin C, cephalexin, cefaclor, cefamandole, ciprofloxacin, bisphosphonates, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, magainins, cathelocedins and defensins.

In some embodiments of the invention, the biologically active agent comprises an anti-inflammatory agent. According to the invention, suitable anti-inflammatory agents include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclopro­fen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, diflu­prednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol pro­pionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

In some embodiments of the invention, the biologically active agent comprises a statin, i.e. a HMG-CoA reductase inhibitor. According to the invention, suitable statins include, without limitation, atorvastatin (Lipitor®), cerivastatin, flu­vastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

In some embodiments of the invention, the biologically active agent comprises chitosan.

Artificial Skeletal Constructs

In a preferred embodiment of the invention, the artificial skeletal constructs comprise porous, bioresorbable, osteoinductive and osteoconductive constructs that are formed with the ECM based bone substitute material described above. According to the invention, the skeletal constructs can be formed in various shapes and can be employed to replace an entire mammalian bone, e.g., rib, or a portion thereof, e.g., sacrum. The skeletal constructs can also be employed to support damages or diseased bones, e.g., bone grafts or overlays.

As indicated above, in some embodiments of the invention, the skeletal construct comprises a continuous bioresorbable osteoinductive construct member formed from a osteoinductive composition comprising a base material and an extracellular matrix (ECM) material, which, when implanted proximate endogenous bone and tissue, induces osteoanagenesis and angiogenesis.

In a preferred embodiment, the base material comprises autogenic bone.

In an alternative embodiment, the base material comprises a degradeable polyurethane; preferably, polycapralactone (Artelon®).

In another alternative embodiment, the base material comprises bone marrow.

Preferably, the ECM material comprises ECM from a mammalian tissue source selected from the group consisting of small intestine submucosa (SIS), urinary bladder submucosa (UBS), stomach submucosa (SS), central nervous system tissue, mesodermal tissue, dermal extracellular matrix, subcutaneous extracellular matrix, gastrointestinal extracellular matrix, tissue surrounding growing bone, placental extracellular matrix, ornomentum extracellular matrix, cardiac extracellular matrix, kidney extracellular matrix, pancreas extracellular matrix, lung extracellular matrix, and combinations thereof.

Preferably, the mammalian tissue source comprises an adolescent mammalian tissue source.

In a preferred embodiment, the osteoinductive composition comprises at least 20% ECM.

In some embodiments of the invention, the osteoinductive composition further comprises at least one of the aforementioned biologically active agents.

In some embodiments, the skeletal construct further includes an outer coating. In some embodiments, the outer coating comprises an osteoinductive composition of the invention. In some embodiments, the outer coating comprises HAp.

Figure 1:
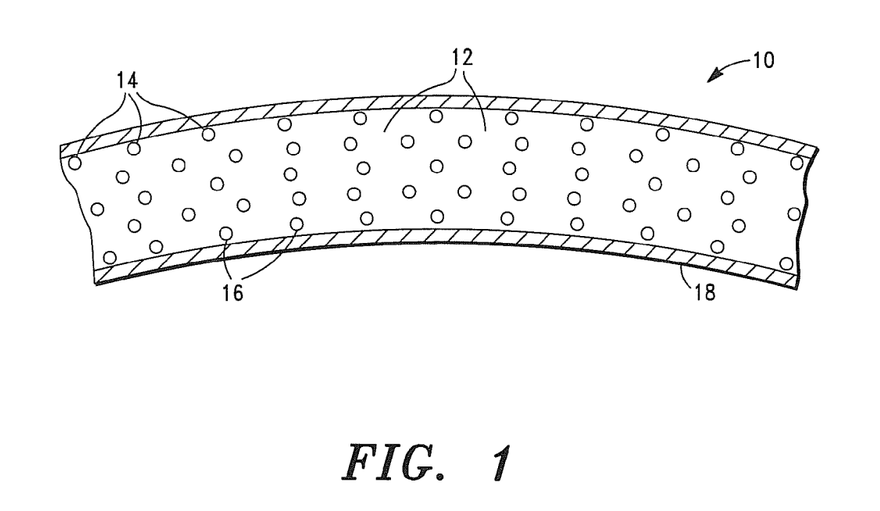
FIG. 1 is a partial side, longitudinal cross-section of one embodiment of a skeletal construct, in accordance with the invention.
Figure 2:
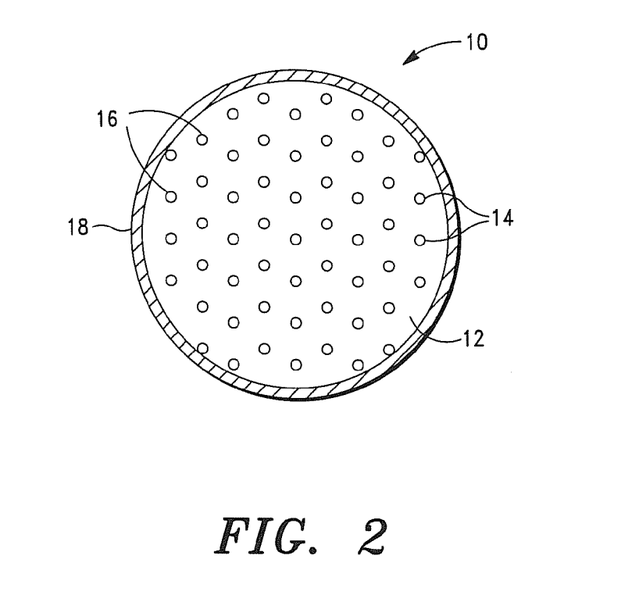
FIG. 2 is a side or end plan view of the skeletal construct shown in FIG. 1, in accordance with the invention.

Referring now to FIGS. 1 and 2, there is shown another embodiment of a skeletal construct of the invention. The skeletal construct 10 similarly comprises a osteoinductive composition of the invention, as described in detail above.

However, as illustrated in FIG. 1, in this embodiment, the skeletal construct 10 comprises a composite structure having a cancellous portion 14 and a continuous cortical portion 12, i.e. a portion of the skeletal construct 10 that functions in a load-bearing capacity.

As illustrated in FIGS. 1 and 2, the cancellous portion 14 includes a plurality of pores 16. In a preferred embodiment, the pores 16 are at least partially interconnected, i.e. interconnected porosity.

In some embodiments, the plurality of pores 16 in the cancellous portion 14 have an average pore size in the range of approximately 5-200 microns. In some embodiments, the average pore size of the cancellous portion 14 is in the range of approximately 30-120 microns. In a preferred embodiment, the average pore size of the cancellous portion 14 is in the range of approximately 50-90 microns.

In a preferred embodiment of the invention, at least 50% of the pores 16 contain at least one of the aforementioned pharmacological or biologically active agents, alone or in combination with an ECM based bone substitute material of the invention.

In a preferred embodiment, the skeletal construct 10 further comprises a crystalline HAp coating 18 on an outer surface thereof.

In a preferred embodiment of the invention, the skeletal construct 10 has a minimum compressive strength of approximately 40 MPa. In some embodiments, the skeletal construct 10 has a compressive strength in the range of approximately 40-200 MPa.

In a preferred embodiment of the invention, the skeletal construct 10 has a minimum modulus of elasticity (or Young's modulus) of approximately 5 MPa. In some embodiments of the invention, the skeletal construct 10 has a modulus of elasticity in the range of approximately 5-12 MPa.

In some embodiments of the invention, the skeletal construct 10 is coated with a bioactive composition of the invention.

In some embodiments of the invention, the skeletal construct 10 is coated with crystalline HAp.

As will readily be appreciated by one having ordinary skill in the art, the present invention provides numerous advantages compared to prior art prosthetic valves. Among the advantages are the following:

The provision of ECM based osteoinductive, biodegradable bone substitute material that promotes osteoanagenesis.

The provision of ECM based bone substitution material that is suitable for use in bone morphogenesis.

The provision of ECM based bone substitution material that exhibits satisfactory biocompatibility, osteoinductivity, osteoconductivity, biodegradability, with freedom from immunogenicity and toxicity to tissues.

The provision of ECM based biodegradable bone substitute material that promotes angiogenesis.

The provision of artificial bioresorbable, osteoconductive and osteoinductive skeletal constructs that promote angiogenesis.

The provision of artificial bioresorbable, osteoconductive and osteoinductive skeletal constructs that function as delivery platforms for pharmacological agents and compositions.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A prosthetic skeletal construct, comprising:
a bioresorbable construct comprising an osteoinductive composition, said osteoinductive composition comprising autogenic bone marrow and acellular extracellular matrix (ECM) from a mammalian tissue source, said construct member being configured to induce osteoanagenesis and angiogenesis when said construct member is implanted proximate endogenous bone and tissue.

2. The skeletal construct of claim 1, wherein said osteoinductive composition further comprises polyurethane urea.

3. The skeletal construct of claim 1, wherein said osteoinductive composition comprises at least 20% of said ECM.

4. The skeletal construct of claim 1, wherein said osteoinductive composition comprises at least 50% of said ECM.

5. The skeletal construct of claim 1, wherein said comprises small intestine submucosa (SIS).

6. The skeletal construct of claim 1, wherein said mammalian tissue source comprises an adolescent mammalian tissue source.

7. The skeletal construct of claim 1, wherein said osteoinductive composition further comprises at least one exogenously added biologically active agent.

8. The skeletal construct of claim 7, wherein said biologically active agent comprises an osteogenic agent selected from the group consisting of TGF-β1, TGF-β2, TGF-β3, TGF-β4, and TGF-β5.

* * * * *